(12) United States Patent
Murugesan (10) Patent No.: US 10,517,601 B2
(45) Date of Patent: Dec. 31, 2019

(54) SURGICAL STAPLING DEVICE WITH FIRING INDICATOR OF UNITARY CONSTRUCTION

(71) Applicant: Covidien LP, Mansfield, MA (US)

(72) Inventor: Ganesan Murugesan, Minhang District (CN)

(73) Assignee: Covidien LP, Mansfield, MA (US)

( * ) Notice: Subject to any disclaimer, the term of this patent is extended or adjusted under 35 U.S.C. 154(b) by 255 days.

(21) Appl. No.: 15/550,817

(22) PCT Filed: Feb. 15, 2015

(86) PCT No.: PCT/CN2015/073114
§ 371 (c)(1),
(2) Date: Aug. 14, 2017

(87) PCT Pub. No.: WO2016/127433
PCT Pub. Date: Aug. 18, 2016

(65) Prior Publication Data
US 2018/0028188 A1 Feb. 1, 2018

(51) Int. Cl.
*A61B 17/115* (2006.01)
*A61B 90/00* (2016.01)
*A61B 17/00* (2006.01)

(52) U.S. Cl.
CPC . *A61B 17/1155* (2013.01); *A61B 2017/00862* (2013.01); *A61B 2090/034* (2016.02); *A61B 2090/0812* (2016.02)

(58) Field of Classification Search
CPC ........ A61B 17/1155; A61B 2090/0811; A61B 2090/034; A61B 2090/0812;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

European Search Report dated Nov. 22, 2018 issued in EP Appln. No. 15881595.
(Continued)

*Primary Examiner* — Andrew M Tecco
*Assistant Examiner* — Nicholas E Igbokwe
(74) *Attorney, Agent, or Firm* — Carter, DeLuca & Farrell LLP (57) ABSTRACT

An indicator (26) includes an indicator body portion (50), a pivot support member (52), a resilient lever (54) and an anchor (66). The pivot support member (52) has a first end (52a) secured to the indicator body portion (50) and a second end (52b) secured to a first end (54a) of the resilient lever (54). The resilient lever (54) has a second end (54b) secured to the anchor (66). The pivot support member (52) is adapted to be pivotally mounted to a body portion (18) of a surgical device and the anchor (66) is adapted to be secured to the surgical device such that pivotal movement of the indicator body portion (50) from a first position to a second position effects movement of the resilient lever (54) from a relaxed configuration to a stressed configuration. In the stressed configuration, the resilient lever (54) urges the indicator body portion (50) towards the first position. The indicator body portion (50) can be integrally molded of a plastic material to define a single part of unitary construction.

18 Claims, 3 Drawing Sheets

(58) Field of Classification Search
CPC ........ A61B 17/068; A61B 2017/00371; A61B 2017/07257; A61B 2090/3616
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A * | 4/1993 | Brinkerhoff ......... A61B 17/115 227/179.1 |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafrtta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |

(56) References Cited

U.S. PATENT DOCUMENTS

| | | | |
|---|---|---|---|
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 * | 12/2007 | Milliman ............. A61B 17/115 227/175.1 |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |

(56) References Cited

U.S. PATENT DOCUMENTS

| | | |
|---|---|---|
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0023325 A1* | 2/2005 | Gresham ............ A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0097025 A1* | 5/2006 | Milliman ............ A61B 17/115 227/175.1 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0049950 A1 | 3/2007 | Theroux et al. |
| 2007/0060952 A1 | 3/2007 | Roby et al. |
| 2009/0230170 A1* | 9/2009 | Milliman ........... A61B 17/0686 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0051669 A1* | 3/2010 | Milliman ............ A61B 17/115 227/175.2 |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0006102 A1* | 1/2011 | Kostrzewski ........ A61B 17/115 227/176.1 |
| 2011/0011916 A1 | 1/2011 | Levine |
| 2011/0095070 A1* | 4/2011 | Patel ................... A61B 17/115 227/181.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |

(56) References Cited

U.S. PATENT DOCUMENTS

| | | |
|---|---|---|
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1* | 10/2013 | Ma .......................... A61B 1/04 227/176.1 |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0319206 A1* | 11/2017 | Zhan .................. A61B 17/1155 |
| 2017/0348002 A1* | 12/2017 | Murugesan ........ A61B 17/1155 |

FOREIGN PATENT DOCUMENTS

| | | |
|---|---|---|
| CN | 103462663 A | 12/2013 |
| CN | 104042288 A | 9/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | WO02080781 A2 | 10/2002 |
| WO | 2008/107918 A1 | 9/2008 |
| WO | 2014139440 A1 | 9/2014 |

OTHER PUBLICATIONS

International Search Report for PCT/CN2015/073114 date of completion is Nov. 6, 2015 (5 pages).

* cited by examiner

SURGICAL STAPLING DEVICE WITH FIRING INDICATOR OF UNITARY CONSTRUCTION

CROSS-REFERENCE TO RELATED APPLICATIONS

This application is a National Stage Application of PCT/CN2015/073114 under 35USC § 371 (a), the disclosures of the above-identified application is hereby incorporated by reference in its entirety.

BACKGROUND

1. Technical Field

The present disclosure relates to surgical stapling devices having a firing indicator. More particularly, the present disclosure relates to circular stapling devices having a firing indicator of unitary construction.

2. Background of Related Art

Surgical devices having an end effector configured to clamp and suture tissue are well known in the medical arts. Typically, these devices include a first jaw which supports an anvil and a second jaw which supports a cartridge which houses a plurality of staples. The first and second jaws are movable in relation to each other between spaced and approximated positions to clamp tissue between the jaws prior to firing the staples into the tissue. To prevent firing the staples before the jaws have been approximated to within a "firing zone", i.e., before the jaws have been approximated sufficiently to effect proper staple formation, it is known to provide a lockout and/or an indicator on the surgical device. Typically, the lockout prevents actuation of a firing trigger until the jaws are approximated to within the firing zone, whereas the indicator provides a visual indication that the jaws are approximated within the firing zone.

Known indicators on surgical stapling devices which provide a visual indication that the jaws are approximated to within the firing zone can include multiple components and be overly complex. A need exists in the medical arts for a simple, inexpensive device for identifying when the jaws of the stapling device have been approximated to within the firing zone.

SUMMARY

One aspect of the present disclosure is directed to a surgical stapling device including a handle assembly having a body portion defining a grip, a rotation knob and an indicator. An elongated body portion extends distally from the handle assembly. An end effector is supported on a distal end of the elongated body portion and includes a cartridge assembly and an anvil assembly. The surgical stapling device includes an approximation assembly having a drive screw movably supported within the handle assembly and an anvil retainer operably connected to the drive screw. The anvil retainer is configured to support the anvil assembly and the drive screw is operably engaged with the rotation knob such that actuation of the rotation knob effects movement of the anvil assembly in relation to the cartridge assembly between spaced and approximated positions. A screw stop is secured to the drive screw. The indicator is of unitary construction and includes an indicator member, a pivot support member, a resilient lever and an anchor. The pivot support member has a first end secured to the indicator member and a second end secured to a first end of the resilient lever. The resilient lever has a second end secured to the anchor. The pivot support member is pivotally secured to the body portion of the handle assembly and the anchor is fixed within the body portion of the handle assembly such that pivotal movement of the indicator member from a first position to a second position effects movement of the resilient lever from a relaxed configuration to a stressed configuration, wherein in the stressed configuration, the resilient lever urges the indicator member towards the first position.

In embodiments, the screw stop includes a block which is positioned to engage the indicator when the anvil assembly moves from the spaced position to the approximated position to pivot the indicator member from the first position to the second position. The block can be formed on an upper surface of the screw stop.

In some embodiments, the resilient lever is positioned to move the indicator member from the second position to the first position when the anvil assembly is moved from the approximated position to the spaced position.

In embodiments, the pivot support member is positioned between the indicator member and the resilient lever and defines a bore which receives a pivot member. The pivot member can be supported on an inner wall of the body portion of the handle assembly.

In certain embodiments, the anchor is supported on an end of the resilient lever opposite the pivot support member and defines a bore which receives a support pin extending from the inner wall of the body portion of the handle assembly.

In some embodiments, the resilient lever includes a pleated, expansible body.

In certain embodiments, the indicator member includes indicia which provides an indication to a clinician of the status of the surgical stapling device.

In embodiments, the body portion of the handle assembly defines a window and the indicator member is positioned beneath the window to facilitate visualization of at least a portion of the indicia.

In some embodiments, the indicia includes a red stripe positioned on a green surface. The red stripe is visible through the window when the indicator member is in the first position and the green surface is visible through the window when the indicator member is in the second position.

In embodiments, the indicator assembly is integrally molded from a plastic material.

Another aspect of the present disclosure includes an indicator of unitary construction. The indicator includes an indicator member, a pivot support member, a resilient lever and an anchor. The pivot support member has a first end secured to the indicator member and a second end secured to a first end of the resilient lever. The resilient lever has a second end secured to the anchor. The pivot support member is adapted to be pivotally mounted to a body of a surgical device and the anchor is adapted to be secured to the surgical device such that pivotal movement of the indicator member from a first position to a second position effects movement of the resilient lever from a relaxed configuration to a stressed configuration, wherein in the stressed configuration, the resilient lever urges the indicator member towards the first position.

In embodiments, the pivot support member is positioned between the indicator member and the resilient lever and defines a bore which is configured to receive a pivot member.

In embodiments, the anchor is supported on an end of the resilient lever opposite the pivot support member and defines a bore which is configured to receive a support pin.

In some embodiments, the resilient lever includes a pleated, expansible body.

In certain embodiments, the indicator member includes indicia to provide an indication to a clinician of the status of a surgical stapling device.

In some embodiments, the indicia includes a red stripe positioned on a green surface.

In some embodiments, the indicator assembly is integrally molded from a plastic material.

BRIEF DESCRIPTION OF THE DRAWINGS

Various embodiments of the presently disclosed surgical stapling device and firing indicator are described herein with reference to the drawings, wherein.

DETAILED DESCRIPTION OF EMBODIMENTS

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

As used herein, the term distal refers to that portion of the device which is farthest from the clinician, while the term proximal refers to that portion of the instrument which is closest to the clinician. In addition, as used herein, the term clinician refers to medical staff including doctors, nurses and support personnel.

Figure 1:
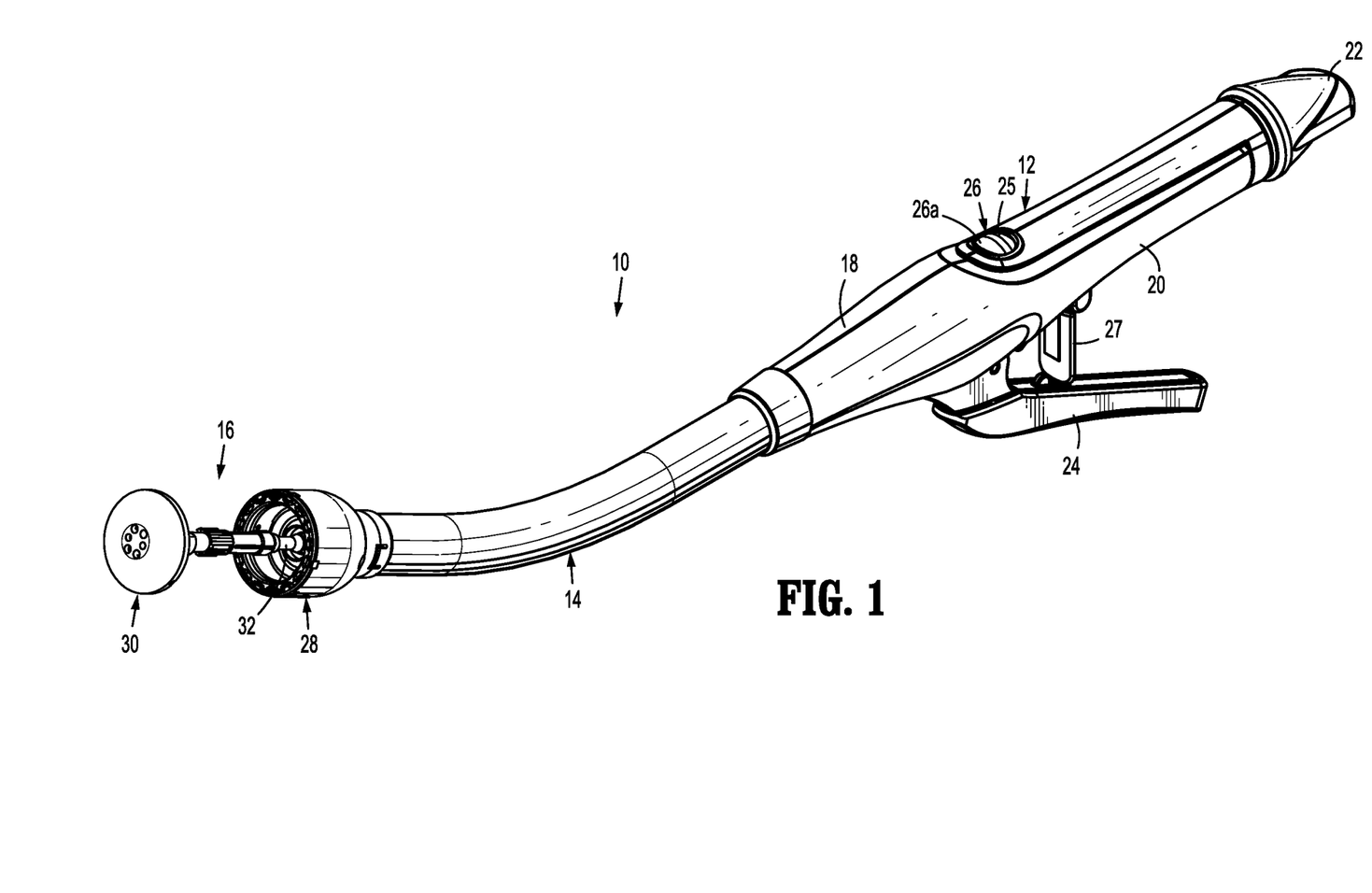
FIG. 1 is a side perspective view of one embodiment of the stapling device of the present disclosure illustrating the stapling device with jaws of the an effector in a spaced configuration.

FIG. 1 illustrates a surgical stapling device 10 having a handle assembly 12, an elongated body portion 14 and an end effector 16. The handle assembly 12 includes a body portion 18 defining a grip 20, a rotation knob 22, a firing trigger 24, and an indicator 26. The indicator 26 is positioned beneath an opening or window 25 formed in the body portion 18 which allows visualization of the indicator 26 by a clinician. A lens 26a can be supported above the indicator 26 to improve visibility of the indicator 26. A firing lockout 27 is pivotally supported on the body portion 18 of the handle assembly adjacent the firing trigger 24, as known in the art, to prevent actuation of the firing trigger 24 until the end effector 16 is moved to an approximated position as will be discussed in further detail below.

The elongated body portion 14 is tubular and extends distally from the body portion 18 of the handle assembly 12. The end effector 16 is supported on a distal end of the elongated body portion 14 and includes a cartridge or shell assembly 28 and an anvil assembly 30. The anvil assembly 30 is supported on an anvil retainer 32 which defines a distal end of an approximation assembly (not shown) of the stapling device 10. The anvil retainer 32 is operably connected to the rotation knob 22 such that rotation of the actuation knob 22 reciprocates the anvil retainer 32 within the elongated body portion 14 to move the anvil assembly 30 in relation to the cartridge assembly 28 between spaced and approximated positions. U.S. Pat. No. 7,303,106 ("the '106 patent") to Milliman et al., discloses a surgical stapling device similar in many respects to surgical stapling device 10. The '106 patent describes firing and approximation mechanisms suitable for use with stapling device 10 and is incorporated herein by reference in its entirety.

Figure 2:
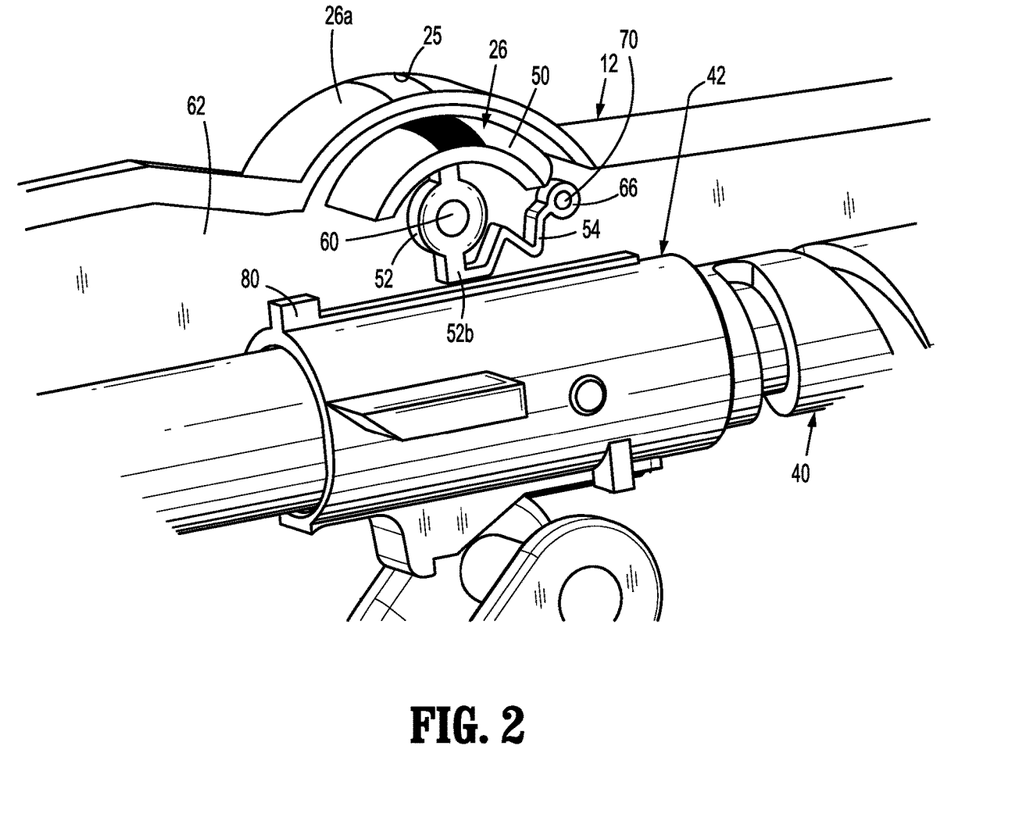
FIG. 2 is a side perspective view of a portion of a handle assembly of the stapling device shown in FIG. 1 with a half-section of the housing removed and illustrating an indicator supported within the housing in a first position adjacent a screw stop of the stapling device.

Referring to FIG. 2, the approximation mechanism of the surgical stapling device 10 includes a drive screw 40 which supports a screw stop 42. The drive screw 40 has a proximal end which is operably connected to the rotation knob 22 (FIG. 1) and a distal end operably connected to the anvil retainer 32 (FIG. 1). The drive screw 40 is linearly movable within the handle assembly 12 in response to rotation of the rotation knob 22 to effect linear movement of the anvil retainer 32 within the cartridge 28. The screw stop 42 is fixedly secured to the drive screw 40 such that movement of the drive screw 40 effects corresponding movement of the screw stop 42. The '106 patent, which has been incorporated herein by reference in its entirety, discloses an approximation mechanism including a screw and screw stop as discussed above.

The indicator 26 is of unitary construction and includes an arcuate indicator body portion 50, a pivot support member 52 and a resilient lever 54. It is envisioned that the indicator body portion 50 may assume a variety of configurations other than arcuate, e.g., flat, concave, convex, spherical, etc. The pivot support member 52 has one end 52a formed with and extending from a bottom of the indicator body portion 50, a second end 52b connected to one end 54a of the resilient lever 54 and a central portion 56 defining a bore 58 that receives a pivot member 60. The pivot member 60 can be integrally formed on an inner wall 62 of the body portion 18 of the handle assembly 12 and pivotally supports the indicator 26 within the body portion 18 beneath the lens cover 26a. Alternately, the pivot member 60 can be formed separately from the body portion 18 of the handle assembly 12.

As discussed above, the resilient lever 54 is integrally formed with the pivot support member 52. A second end 54b end of the resilient lever 54 positioned opposite to the pivot support member 52 defines an anchor 66 defining bore 68 which receives a support pin 70. The support pin 70 can be formed on an inner wall 62 of the body portion 18 of the handle assembly 12 and fixedly secures the end 54b of the resilient lever 54 to the body portion 18 of the handle assembly 12.

The resilient lever 54 includes a pleated, expansible body 74 that extends between the anchor 66 and the pivot support member 52. The expansible body 74 is movable from a relaxed configuration shown in FIGS. 2 and 3 to a compressed or stressed configuration shown in FIG. 5 as will be discussed in detail below. As discussed above, the pivot support member 52 and the end 54b of the resilient lever 54 are secured and axially fixed in relation to the body portion 18 of the handle assembly 12. As such, when the indicator body portion 50 is pivoted in a counter-clockwise direction as viewed in FIG. 3, the end 52b of the pivot support member pivots toward the anchor 66 to compress the expansible body 74 of the resilient lever 54 to the stressed configuration (FIG. 5).

Figure 4:
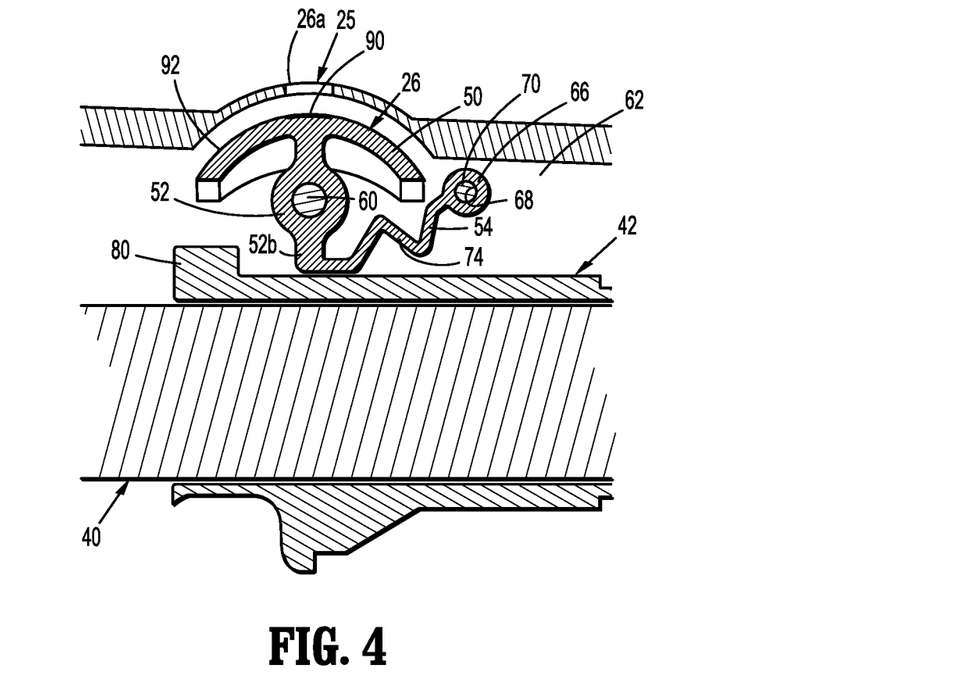
FIG. 4 is a side cross-sectional view of the indicator and screw stop shown in FIG. 2 in the first position.
Figure 5:
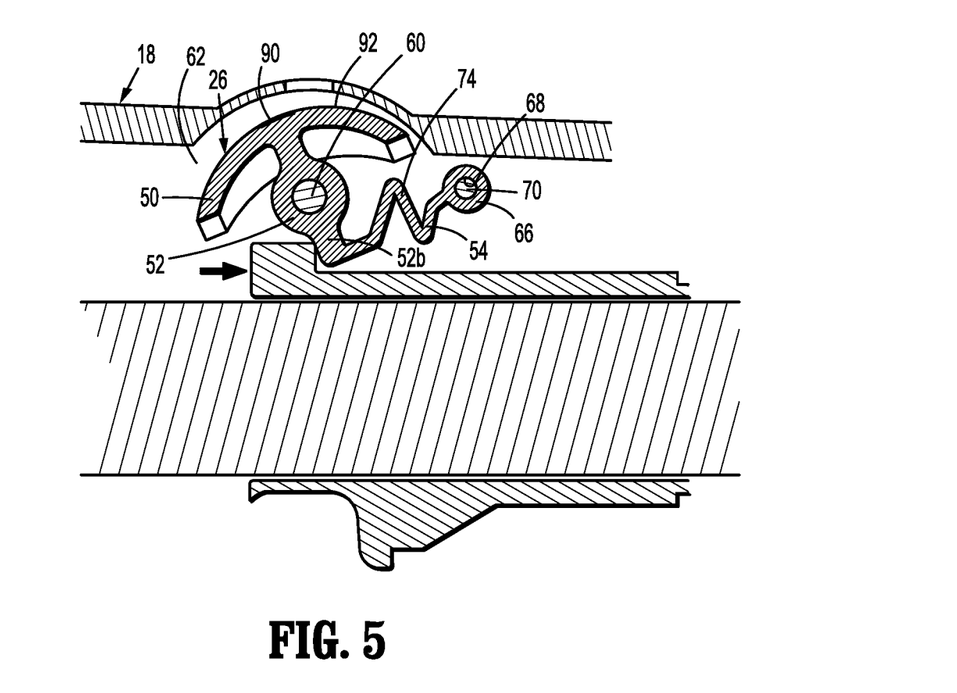
FIG. 5 is a side cross-sectional view of the indicator and screw stop shown in FIG. 4 after the screw stop is moved into engagement with the indicator and the indicator is moved to a second position.

Referring to FIGS. 1, 4 and 5, the screw stop 42 is fixedly supported on the drive screw 40 of the stapling device 10 and includes an engagement member, e.g., a block 80, which is positioned to engage the second end 52b of the pivot support member 52 of the indicator 26. In embodiments, the second end 52b of the pivot support member 52 can include a rib or the like which is positioned to engage the block 80 of the screw stop 42.

Referring to FIG. 4, when the anvil assembly 30 is spaced from the cartridge assembly 28 (FIG. 1), the screw stop 42 is positioned such that the block 80 is positioned distally of the second end 52b of the pivot support member 52. As discussed above, as is known in the medical arts, the screw stop 42 is axially fixed to the drive screw 40 and the drive screw 40 is operably coupled to the anvil assembly 30 and to the rotation knob 22.

Referring to FIG. 5, when the rotation knob 22 (FIG. 1) is actuated, i.e., rotated by a clinician, the drive screw 40 is retracted within the body portion 18 of the handle assembly 12 to retract the anvil retainer 32 into the cartridge assembly 28 and to move the anvil assembly 30 towards the cartridge assembly 28 to the approximated position. As the drive screw 40 is retracted within the handle assembly 12 of the stapling device 10 to move the anvil assembly 30 towards the approximated position, the block 80 of the screw stop 42 engages the second end 52b of the pivot support member 52. Upon continued retraction of the drive screw 40 and screw stop 42, the block 80 of the screw stop 42 pivots the pivot support member 52 about the pivot member 60 to pivot the indicator member 50 from a first position beneath the window 25 to a second position beneath the window 25.

Figure 3:
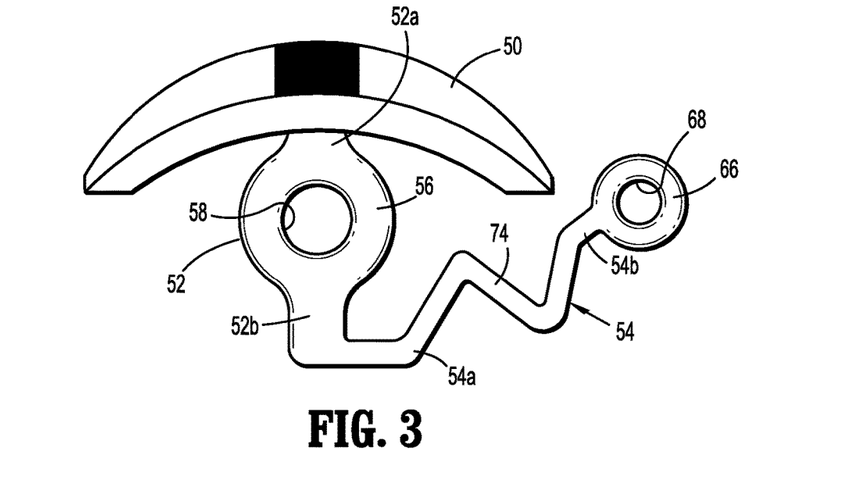
FIG. 3 is a side view of the indicator shown in FIG. 2.

Referring also to FIG. 3, the indicator body portion 50 includes indicia which provide an indication to the clinician of the status of the stapling device 10. More specifically, the indicia may be in the form of a red stripe 90 positioned on a green upper surface 92 of the indicator body portion 50. When the indicator body portion 50 is in the first position (FIG. 4) and the red stripe 90 is aligned with the window 25, the red stripe 90 indicates to a clinician that the end effector 16 or anvil 30 of the end effector 16 is in a spaced or unapproximated position and thus, the stapling device 10 is not in a fire-ready position. When the indicator body portion 50 is pivoted to the second position (FIG. 5) in response to retraction of the drive screw 40 and screw stop 42 within the body portion 18 of the handle assembly 12, the green upper surface 92 of the indicator body portion 50 becomes visible through the window 25 of the stapling device 10 and indicates to the clinician that the stapling device 10 is in a fire ready position.

It is envisioned that the indicia may be selected from a variety of different colors, characters or the like.

It is noted that as the pivot support member 52 is pivoted towards the expansible body 74 of the resilient lever 54, the resilient lever 54 is moved to the stressed or compressed configuration. As such, when the anvil assembly 30 is moved from the approximated position towards the spaced position via actuation of the rotation knob 22, the expansible body 74 returns to its relaxed configuration to pivot the indicator member 50 back the first position.

The indicator member 26 can be molded as a single, integral, unitary part from a plastic material such as nylon or polyvinyl chloride (PVC) By providing an indicator of unitary construction, the number of components and the complexity of the handle assembly can be minimized to reduce cost.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   a handle assembly including a body portion defining a grip, a rotation knob and an indicator;
   an elongated body portion extending distally from the handle assembly;
   an end effector supported on a distal end of the elongated body portion, the end effector including a cartridge assembly and an anvil assembly;
   an approximation assembly including a drive screw movably supported within the handle assembly and an anvil retainer operably connected to the drive screw, the anvil retainer being configured to support the anvil assembly and the drive screw being operably engaged with the rotation knob such that actuation of the rotation knob effects movement of the anvil assembly in relation to the cartridge assembly between spaced and approximated positions; and
   a screw stop secured to the drive screw;
   wherein the indicator is of unitary construction and includes an indicator body portion, a pivot support member, a resilient lever and an anchor, the pivot support member having a first end secured to the indicator body portion and a second end secured to a first end of the resilient lever, the resilient lever having a second end secured to the anchor, the pivot support member being pivotally secured to the body portion of the handle assembly and the anchor being fixed within the body portion of the handle assembly such that pivotal movement of the indicator body from a first position to a second position effects movement of the resilient lever from a relaxed configuration to a stressed configuration, wherein in the stressed configuration, the resilient lever urges the indicator body portion towards the first position.

2. The surgical stapling device according to claim 1, wherein the screw stop includes a block which is positioned to engage the indicator to pivot the indicator body portion from the first position to the second position when the anvil assembly moves from the spaced position to the approximated position.

3. The surgical stapling device according to claim 2, wherein the resilient lever is positioned to move the indicator body portion from the second position to the first position when the anvil assembly is moved from the approximated position to the spaced position.

4. The surgical stapling device according to claim 2, wherein the block is formed on an upper surface of the screw stop.

5. The surgical stapling device according to claim 1, wherein the pivot support member is positioned between the indicator body portion and the resilient lever and defines a bore which receives a pivot member, the pivot member being supported on an inner wall of the body portion of the handle assembly, the anchor being supported on an end of the resilient lever opposite the pivot support member.

6. The surgical stapling device according to claim 1, wherein the anchor defines a bore which receives a support pin extending from the inner wall of the body portion of the handle assembly.

7. The surgical stapling device according to claim 1, wherein the resilient lever includes a pleated, expansible body.

8. The surgical stapling device according to claim 1, wherein the indicator body portion includes indicia which provides an indication to a clinician of the status of the surgical stapling device.

9. The surgical stapling device according to claim 8, wherein the body portion of the handle assembly defines a window, the indicator body portion being positioned beneath the window to facilitate visualization of at least a portion of the indicia.

10. The surgical stapling device according to claim 9, wherein the indicia includes a red stripe positioned on a green surface, the red stripe being visible through the window when the indicator body portion is in the first position and the green surface being visible through the window when the indicator body portion is in the second position.

11. The surgical stapling device according to claim 1, wherein the indicator assembly is integrally molded from a plastic material.

12. An indicator of unitary construction comprising:
an indicator body portion, a pivot support member, a resilient lever and an anchor, the pivot support member having a first end secured to the indicator body portion and a second end secured to a first end of the resilient lever, the resilient lever having a second end secured to the anchor, the pivot support member being adapted to be pivotally mounted to a surgical device and the anchor adapted to be secured to the surgical device such that pivotal movement of the indicator body portion from a first position to a second position effects movement of the resilient lever from a relaxed configuration to a stressed configuration, wherein in the stressed configuration, the resilient lever urges the indicator body portion towards the first position.

13. The indicator according to claim 12, wherein the pivot support member is positioned between the indicator body portion and the resilient lever and defines a bore which is configured to receive a pivot member.

14. The indicator according to claim 12, wherein the anchor defines a bore which is configured to receive a support pin.

15. The indicator according to claim 12, wherein the resilient lever includes a pleated, expansible body.

16. The indicator according to claim 12, wherein the indicator body portion includes indicia to provide an indication to a clinician of the status of a surgical stapling device.

17. The indicator according to claim 16, wherein the indicia includes a red stripe positioned on a green surface.

18. The indicator according to claim 12, wherein the indicator assembly is integrally molded from a plastic material.

* * * * *